United States Patent
Saigusa et al.

(10) Patent No.: US 7,826,590 B2
(45) Date of Patent: Nov. 2, 2010

(54) APPARATUS AND METHOD FOR X-RAY PHOTOGRAPHING A TIRE

(75) Inventors: Shigenobu Saigusa, Utsunomiya (JP); Tatsuya Hasi, Hikone (JP); Ryo Takasu, Kushima (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 12/067,680

(22) PCT Filed: Sep. 20, 2006

(86) PCT No.: PCT/JP2006/318599

§ 371 (c)(1),
(2), (4) Date: Jun. 9, 2009

(87) PCT Pub. No.: WO2007/034814

PCT Pub. Date: Mar. 29, 2007

(65) Prior Publication Data

US 2009/0285359 A1     Nov. 19, 2009

(30) Foreign Application Priority Data

Sep. 22, 2005  (JP) .............................. 2005-276004

(51) Int. Cl.
*G01N 23/04* (2006.01)
(52) U.S. Cl. ......................................................... 378/61
(58) Field of Classification Search .................... 378/61
See application file for complete search history.

(56) References Cited

U.S. PATENT DOCUMENTS

| | | | | |
|---|---|---|---|---|
| 3,809,900 A | * | 5/1974 | Steffel | 378/61 |
| 4,677,848 A | | 7/1987 | Flory | |
| 5,003,568 A | * | 3/1991 | Steffel | 378/61 |
| 5,083,306 A | * | 1/1992 | Steffel | 378/61 |
| 5,148,456 A | | 9/1992 | Steffel | |

FOREIGN PATENT DOCUMENTS

DE       22 31 792 A1    1/1974

(Continued)

OTHER PUBLICATIONS

Extended European Search Report dated Oct. 13, 2009 (6 pages).

*Primary Examiner*—Chih-Cheng G Kao
(74) *Attorney, Agent, or Firm*—Sughrue Mion, PLLC

(57) ABSTRACT

Regarding a X-ray photographing-tire apparatus and method, defining the reference plane as the plane perpendicular to the center axis of a tire mounted on a rotary device and passing through the X-ray source, and defining the reference line as the line headed from the center axis to the X-ray source within the reference plane, the X-ray source is oriented so that a predetermined azimuth range coincides with a predetermined angular range in which the reference line lies, within the reference plane, and a first line-sensor, being oriented parallel with the center axis, is placed within said predetermined azimuth range, in the radial outside of the tread portion TR of the tire, and the first line-sensor is placed at the position deviated from the plane defined by both reference line and the center axis, having two degrees of freedom of motion within the reference plane with orientation of the receiving surface kept constant.

5 Claims, 5 Drawing Sheets

FOREIGN PATENT DOCUMENTS

| | | |
|---|---|---|
| DE | 2 262 982 A1 | 6/1974 |
| EP | 0 315 099 A2 | 5/1989 |
| JP | 62133342 A | 6/1987 |
| JP | 5131816 A | 5/1993 |
| JP | 2000111501 A | 4/2000 |

* cited by examiner (a)

(b)

(a)

(b)

APPARATUS AND METHOD FOR X-RAY PHOTOGRAPHING A TIRE

TECHNICAL FIELD

This invention relates to an apparatus for X-ray photographing a tire and a method utilizing the apparatus, for inspecting the arrangement of steel cords, etc. by non-destructive observation of the interior of a tire, especially relates to the improvement capable of acquiring excellent image having neither distortion nor blur.

RELATED ART

There is already known an apparatus for X-ray photographing a tire as shown in FIG. 1. FIG. 1(a) is an outlined cross sectional view at the plane including the tire center axis, showing a conventional X-ray photographing-tire apparatus 80 in relation to a large tire to be photographed, and FIG. 1(b) is a cross sectional view corresponding b1-b1 section in FIG. 1(a). X-ray photographing-tire apparatus 80 comprises a rotary device (not shown) to mount and rotate a tire T1 about its center axis C, a point-like X-ray source 82 emitting X-ray in an angular range specified by a predetermined azimuth range α and a predetermined elevation angle range β, and three linear line-sensors 83, 84, 85 detecting one dimensional x-ray intensity distribution.

In FIG. 1(a), the rotary device can be configured to rotate a tire about the axis common to all tire sizes, or it can be configured to rotate a tire about its center axis C allocated at a different position depending on the size of the tire, within the paper plane.

Defining the direction of Z-axis as the direction parallel with the center axis C, defining the reference plane H as the plane perpendicular to the direction of Z-axis, and defining the reference line L as the line headed from Z-axis to the X-ray source within the reference plane H, the X-ray source 82 is oriented so that said predetermined azimuth range α coincides with a predetermined angular range, in which the reference line lies, within the reference plane H, and in order to obtain a image with high resolution, said X-ray source is configured to be movable along on said reference line, so that it can be placed at the nearest position to the inner surface of the tread portion TR of the tire T1 depending on the size of the tire, as long as said predetermined elevation angle range β covers the angular range including both bead cores BC with the tread portion in between.

Light receiving elements are arranged on each of the line-sensors 83, 84, 85 in its longitudinal direction for detecting one dimensional x-ray intensity distribution, and it is recommended that the X-ray incident direction relative to the light receiving surface of the light receiving elements is kept unchanged regardless the size of a tire photographed, for specifying the tire structure precisely based on the one dimensional intensity distribution obtained from line-sensors 83, 84, 85. Therefore, the light receiving surface 83a, 84a, 85a located at the points where the line-sensors 83, 84, 85 intersect with the reference plane H or the plane V, which is perpendicular to one of these line-sensors, are oriented facing the X-ray source 82 perpendicularly, for example, the line-sensor 83 is set so that the angle γ between the light receiving surface 83a and the line headed from the light receiving surface 83a to X-ray source 82, is 90 degree.

The first line-sensor 83 is disposed outside the tread portion TR of the tire T1, in parallel with the center axis C, within said predetermined azimuth range α about the X-ray source 82, and the second and third line-sensors 84, 85 are disposed outside the corresponding sidewalls on the lines formed by moving the reference line L in parallel outwards in the tire lateral direction, respectively.

By emitting X-ray from the X-ray source under the rotation of the tire T1 mounted on the rotary device at a given rotational speed, the line-sensors can detect continuously one-dimensional X-ray intensity distribution of X-ray transmitted through the tire T1. A control device (not shown) is provided in the X-ray photographing-tire apparatus 80, and the control device is configured to take in the information detected by the line-sensors 83, 84, 85, synchronized with the tire rotation, and to produce a transmission X-ray image of the full circumference and full width of the tire, based on this information. In this way, it is made possible to obtain a transmission X-ray image of a whole tire.

FIG. 2(a) is an outlined cross sectional view at a plane of meridian, showing a conventional X-ray photographing-tire apparatus 80 in relation to a tire T2 to be photographed, which is smaller than the tire T1, and FIG. 2(b) is a cross sectional view corresponding b2-b2 section in FIG. 2(a). When photographing a small tire T2, in order to obtain a image with high resolution, the position of the X-ray source is adjusted by moving X-ray source back and forth along on said reference line L, so that it can be placed at the nearest position to the inner surface of the tread portion TR of the tire T1 as long as said predetermined elevation angle range β covers the angular range including both bead cores BC with the tread portion in between, as well. On this occasion, it is preferable that the line-sensors 83, 84, 85 are placed as close as possible to the outer surface of the tire in order to eliminate distortion or blur on the image.

DISCLOSURE OF THE INVENTION

For this purpose, the first line-sensor 83 is configured to be movable close to and away from the center axis C, and the line-sensors 84, 85 are configured to be movable in the direction in parallel with the center axis C, however, it is impossible to move all of the line-sensors 83, 84, 85 to be close to the outer surface of a tire enough to eliminate the occurrence of distortion or blur on the image, because the first line-sensor 83 interferes with the second and third line-sensors 84, 85 on the way, because these line-sensors 83, 84, 85 are placed on the same plane (paper plane in FIG. 2(a)).

In FIG. 2 (a), the positions of the line-sensors 83, 84, 85 corresponding to the smaller tire T2 are represented by solid lines and the positions corresponding to the larger tire T1 are numbered as 83m, 84m, 85m.

This invention has been conceived in view of such a problem, and it is therefore an object of the present invention to provide an apparatus for X-ray photographing a tire and a method utilizing the apparatus, capable of acquiring excellent image of the full circumference and full width of a tire, having no distortion nor blur.

(1) The present invention provides an apparatus for X-ray photographing a tire, the apparatus comprising a rotary device for rotating a tire of any size chosen out of plural sizes with the center axis of the tire parallel with a given direction within a given plane, a point-like X-ray source emitting X-rays in an angular range specified by a predetermined azimuth range and a predetermined elevation angle range, and three linear line-sensors detecting a one dimensional X-ray intensity distribution by means of light receiving elements aligned in the longitudinal direction of each line-sensor, and producing a transmission X-ray image of the full circumference and full width of the tire, based on said one dimensional X-ray intensity distribution detected by said line-sensors for each angular position in tire rotation, characterized in that:

said X-ray source is oriented so that said predetermined azimuth range coincides with a predetermined angular range within a plane perpendicular to said given direction, said predetermined angular range including a reference line which is defined as the line perpendicular to said given direction and passing through the X-ray source, said X-ray source is movable along on said reference line according to the size of the tire mounted on the rotary device, so that said X-ray source can be placed at the nearest position to the inner surface of a tread portion of the tire as long as said predetermined elevation angle range covers the angular range including both bead cores with the tread portion in between, each of said three line-sensors is disposed so that at a plane perpendicular to a longitudinal direction of the respective line sensor and passing through the X-ray source, the light receiving surface of the corresponding light receiving elements is oriented perpendicular to a line headed to the X-ray source, a first line-sensor, being oriented parallel with said given direction, is placed within said predetermined azimuth range, in the radial outside of the tread portion of the tire mounted on the rotary device, second and third line-sensors, being disposed on the line formed by moving said reference line in parallel in said given direction, in the lateral outside of the respective sidewall portions of the tire mounted on the rotary device, the first line-sensor is placed at the position deviated from the plane defined by both said reference line and said center axis, having two degrees of freedom of motion within a plane perpendicular to said given direction, so that the first line-sensor can get as close as possible to the outer surface of the tread portion of the tire, according to the size of the tire mounted on the rotary device, keeping the orientation of said receiving surface of the first line-sensor perpendicular to the line headed to said X-ray source, The second and third line-sensors are movable in the direction parallel with the center axis according to the size of the tire mounted on the rotary device, so that the second and third line-sensors can be as close as possible to respective sidewall portions of the tire.

(2) The present invention further provides a method of manufacturing a tire according to the invention in item (1), wherein said two degrees of freedom of motion pertinent to the first line-sensor comprises a translational degree of freedom along the line formed by moving said reference line in parallel, and a rotational degree of freedom around the line parallel with said given direction.

(3) The present invention further provides a method of manufacturing a tire according to the invention in item (1), wherein the inclination of the light receiving surface of the first line-sensor to said reference line is maintained constant and said two degrees of freedom of motion pertinent to the first line-sensor comprises a translational degree of freedom in the direction parallel with the reference line and a translational degree of freedom in the direction perpendicular to the reference line.

(4) The present invention further provides a method of manufacturing a tire according to the invention in item (1), wherein the inclination of the light receiving surface of the first line-sensor to said reference line is maintained constant and said two degrees of freedom of motion pertinent to the first line-sensor comprises a translational degree of freedom in the direction parallel with the reference line and a translational degree of freedom in the direction close to and away from the X-ray source.

(5) A method for X-ray photographing a tire, the size of which is arbitrarily chosen from a predetermined group of sizes, utilizing the apparatus for X-ray photographing a tire according to any one of the items (1)-(4), wherein said method comprises steps of: setting a tire onto the rotary device with the center axis oriented in said given direction, thereafter moving the X-ray source along on the reference line, so that X-ray source is placed at the nearest position to the inner surface of the tread portion of the tire as long as said predetermined elevation angle range covers the angular range including both bead cores with the tread portion in between, and moving the three line-sensors so that they get as close as possible to the outer surface of the tire, thereafter emitting X-ray from the X-ray source with tire rotating at a given rotational speed, and then finally acquiring transmission X-ray image of the tire.

According to the invention in item (1), the 1st-3rd line-sensors are configured to be movable to come close to the tread portion and the sidewall portions respectively, and the first line-sensor is disposed at the position deviated from the plane within which the second and third line-sensor lie, so that they don't interfere with each other even when they get close to the outer surface of the tire, and in addition, since the first sensor is movable within the reference plane with two degree of freedom of motion, it can be close to the tire with light receiving surface kept perpendicular to the X-ray source.

According to the invention in item (2), said two degrees of freedom of motion pertinent to the first line-sensor comprises a translational degree of freedom along the line formed by moving said reference line in parallel, and a rotational degree of freedom about the line parallel with said given direction, so that the invention in item (1) can be easily achieved.

According to the invention in item (3), said two degrees of freedom of motion pertinent to the first line-sensor comprises a translational degree of freedom in the direction parallel with the reference line and a translational degree of freedom in the direction perpendicular to the reference line, so that the invention in item (1) can be easily achieved as well.

According to the invention in item (4), said two degrees of freedom of motion pertinent to the first line-sensor comprises a translational degree of freedom in the direction parallel with the reference line and a translational degree of freedom in the direction close to and away from the X-ray source, so that the invention in item (1) can be easily achieved, in this case as well.

According to the invention in item (5), after setting a tire onto the rotary device before emitting X-ray, by moving the X-ray source along on the reference line so that X-ray source is placed at the nearest position to the inner surface of the tread portion of the tire, and x-ray can be emitted in the range covering all the area between both bead cores, and by moving the three line-sensors so that they get as close as possible to the outer surface of the tire, it is capable of photographing the full width of the tire, and acquiring the image with no distortion nor blur.

Figure 1:
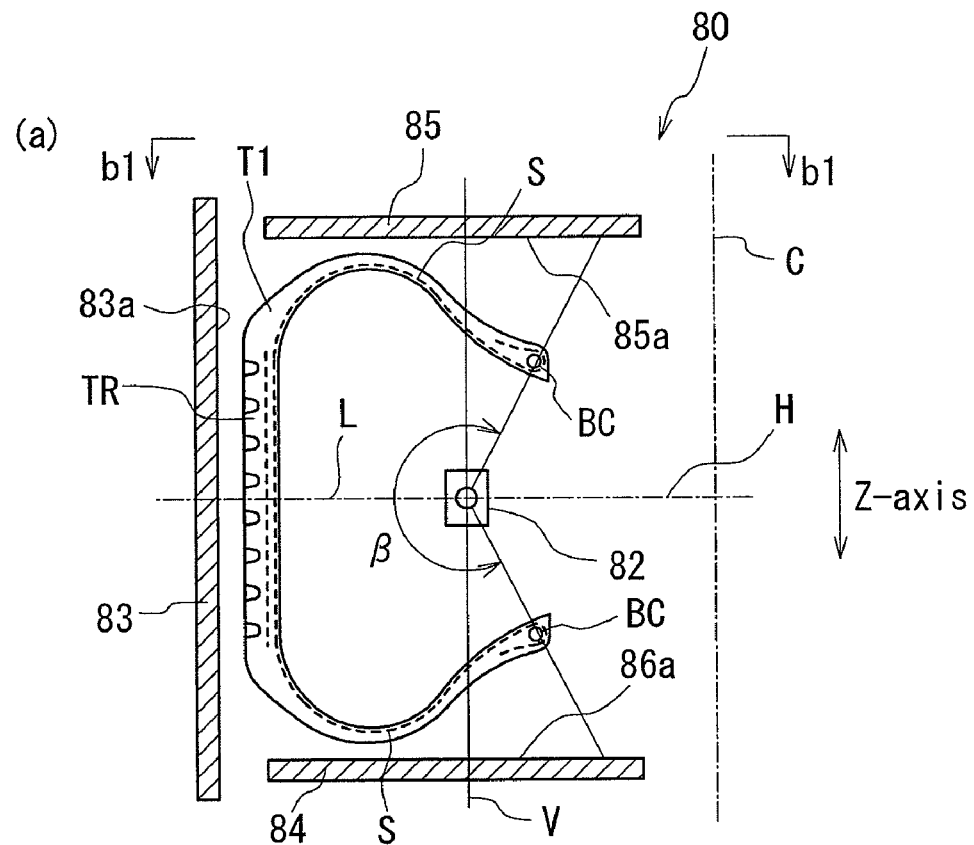
FIG. 1 is outlined cross sectional view showing a conventional X-ray photographing-tire apparatus in relation to a large tire to be photographed.
Figure 1:
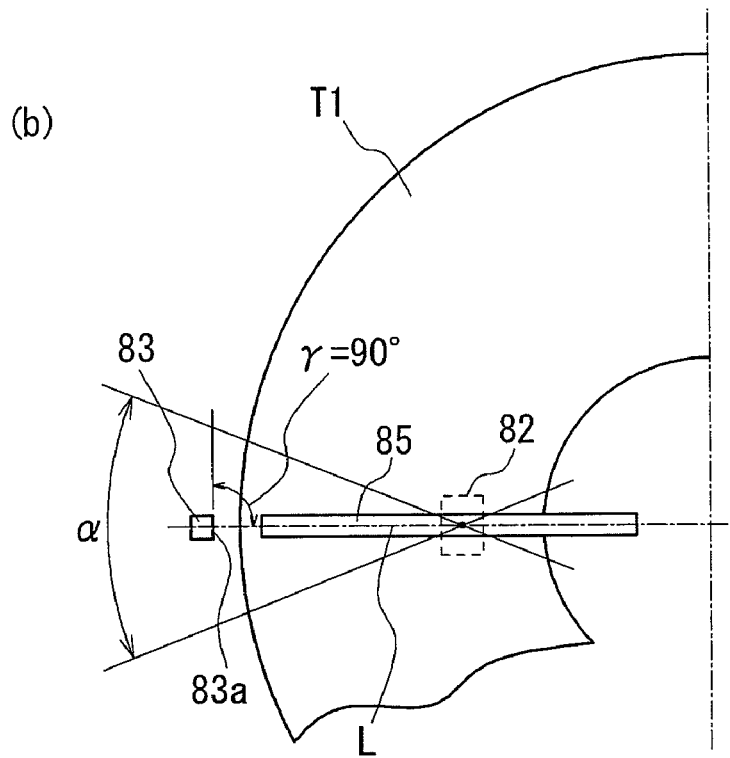
Figure 2:
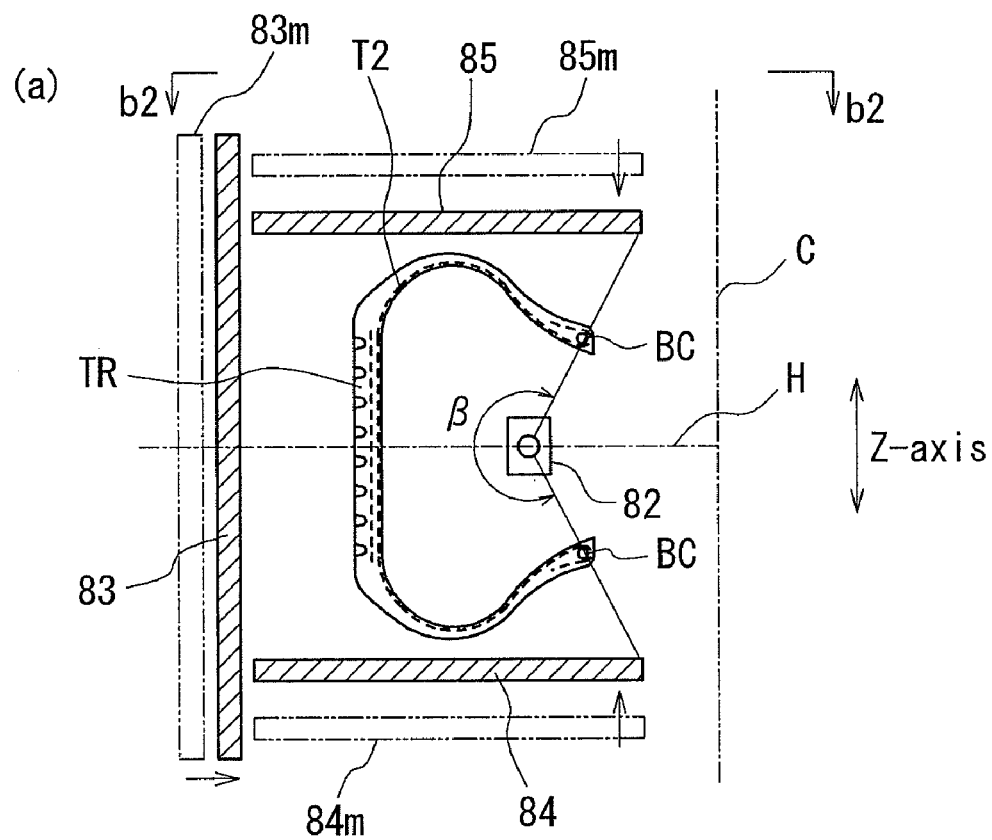
FIG. 2 is outlined cross sectional views showing a conventional X-ray photographing-tire apparatus in relation to a small tire to be photographed.
Figure 2:
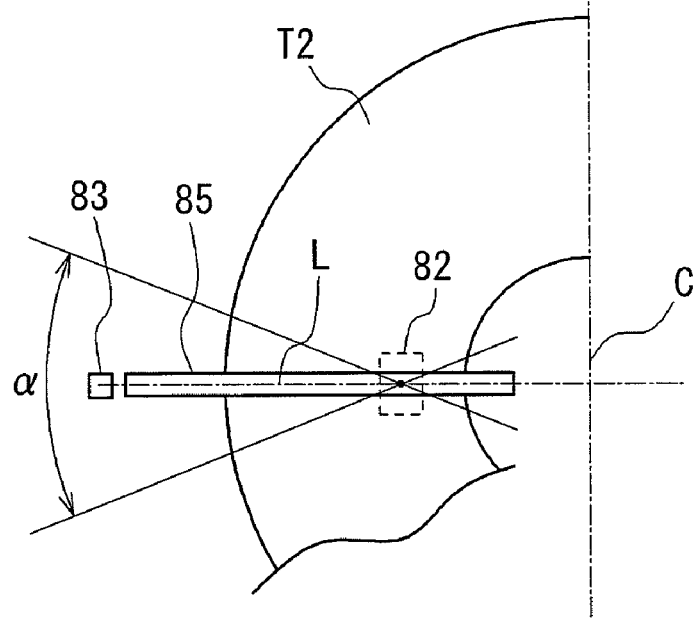

REFERENCE SYMBOLS 1 rotary device (rollers)
2 X-ray source
3 first line-sensor
3a light receiving surface of first line-sensor
3m, 3n, 3p, 3q, 3v, 3w positions of first line-sensor
4 second line-sensor
4a light receiving surface of second line-sensor
4m, 4n positions of second line-sensor
5 third line-sensor
5a light receiving surface of third line-sensor
5m, 5n positions of third line-sensor
10 X-ray photographing-tire apparatus
11 line sensor support-transfer device
12 first-sensor-X-axis-driving portion
13 first-sensor-θ-axis-driving portion
14 second-sensor-Z-axis-driving portion
T, T1, T2 tire
TR tread portion
S sidewall portion

BEST MODE FOR CARRYING OUT THE INVENTION

Figure 3:
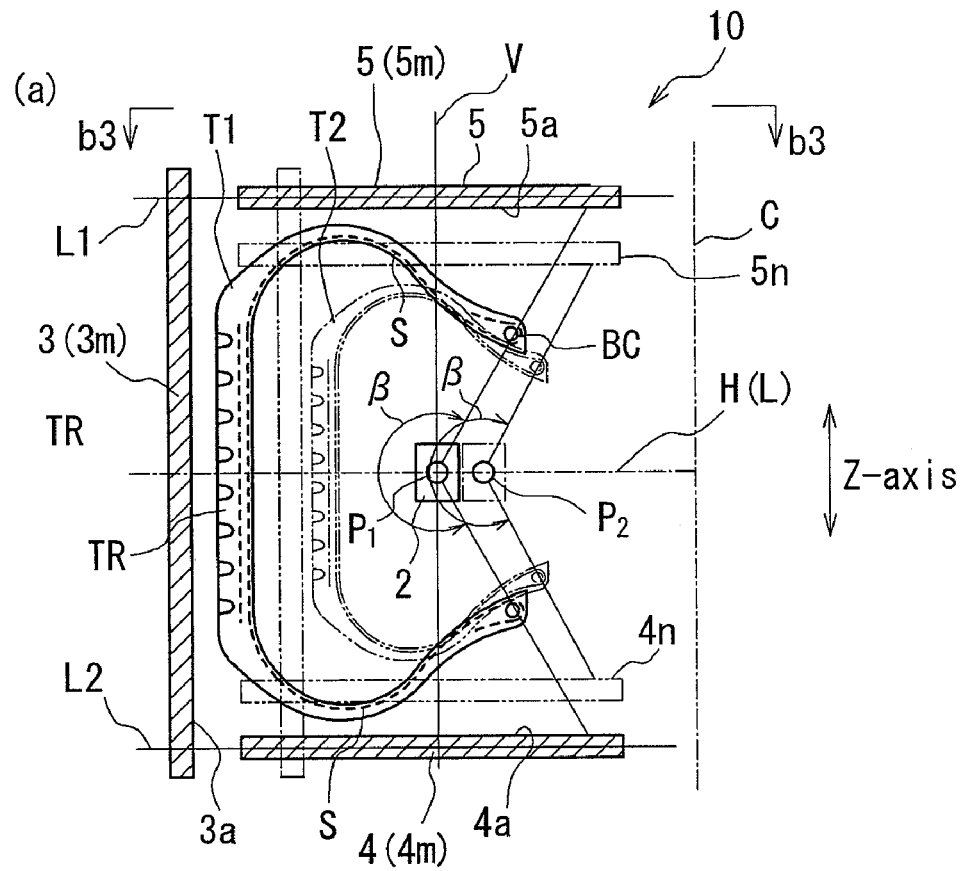
FIG. 3 is outlined cross sectional view showing a X-ray photographing-tire apparatus pertinent to present invention in relation to a tire to be photographed.
Figure 3:
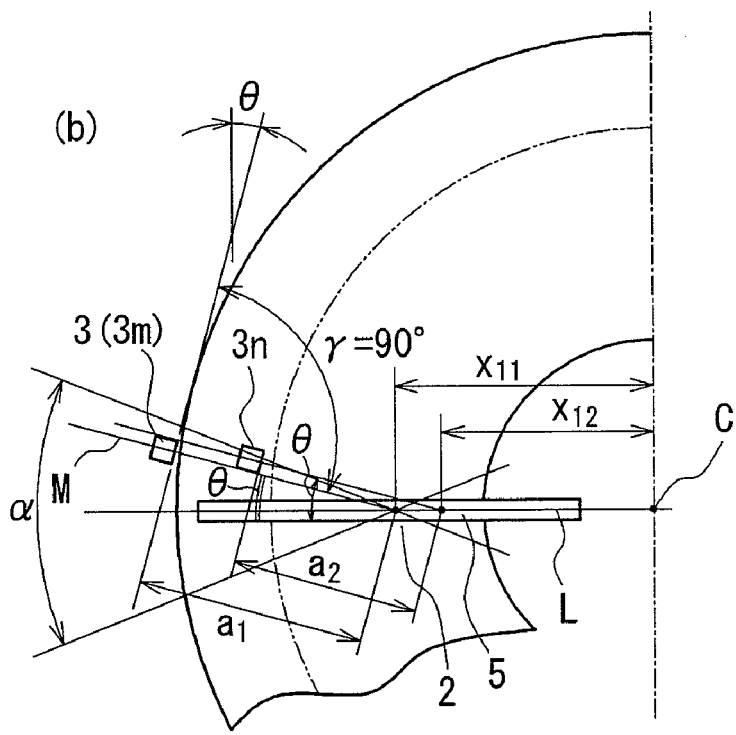

An embodiment of the present invention will be described with reference to the drawings. FIG. 3 (a) is a outlined cross sectional view at the plane including the center axis of the tire, showing a X-ray photographing-tire apparatus 10 in relation to a tire to be photographed, FIG. 1(b) is a cross sectional view corresponding b3-b3 view in FIG. 3(a). X-ray photographing-tire apparatus 10 comprises a rotary device (not shown) to mount and rotate a tire T1 about its center axis C, a point-like X-ray source 2 emitting X-ray in an angular range specified by a predetermined azimuth range α and a predetermined elevation angle range β, and three linear line-sensors 3, 4, 5 detecting one dimensional x-ray intensity distribution by means of light receiving elements aligned in the longitudinal direction.

As explained previously, in FIG. 3(a), the rotary device can be configured to rotate a tire about the axis common to all tire sizes, or it can be configured to rotate a tire about its center axis C allocated at a different position depending on the size of the tire, within the paper plane.

Defining the direction of Z-axis as the direction parallel with the center axis C, defining the reference plane H as the plane perpendicular to the direction of Z-axis, and defining the reference line L as the line headed from Z-axis to the X-ray source within the reference plane H, the X-ray source 2 is oriented so that said predetermined azimuth range α coincides with a predetermined angular range, in which the reference line lies, within the reference plane H, and in order to obtain a image with high resolution, said X-ray source is configured to be movable along on said reference line, so that it can be placed at the nearest position to the inner surface of the tread portion TR of the tire T1 depending on the size of the tire, as long as said predetermined elevation angle range βcovers the angular range including both bead cores BC with the tread portion in between.

In the planes H, V perpendicular to line-sensors 3, 4, 5 and including the X-ray source, the light receiving surfaces of light receiving elements are oriented facing the X-ray source 2 perpendicularly, for example, the line-sensor 3 is set so that the angle γ between the light receiving surface 3a and the line headed from the light receiving surface 3a to X-ray source 2, is 90 degree.

The first line-sensor 3 is disposed outside the tread portion TR of the tire T1, in parallel with the center axis C, within said predetermined azimuth range α about the X-ray source 2, and the second and third line-sensors 4, 5 are disposed outside the corresponding sidewalls on the lines L1, L2 formed by moving the reference line L in parallel in the direction of the center axis, respectively.

By emitting X-ray from the X-ray source under the rotation of the tire T1 mounted on the rotary device at a given rotational speed, the line-sensors can detect continuously one-dimensional X-ray intensity distribution of X-ray transmitted through the tire T1. A control device (not shown) is provided in the X-ray photographing-tire apparatus 10, and the control device is configured to take in the information detected by the line-sensors 3, 4, 5, synchronized with the tire rotation, and to produce a transmission X-ray image of the full circumference and full width of the tire, based on this information. In this way, it is made possible to obtain a transmission X-ray image of a whole tire.

The X-ray photographing-tire apparatus 10 is configured to be capable of photographing a tire of any size chosen from a plurality of different sizes and obtaining a transmission X-ray image of them, and in FIG. 3, two-dot chain lines show the location of a tire T2 which is smaller than tire T1 when it is x-ray photographed. In order to obtain a transmission X-ray image with high resolution for the tire with different size as well, the X-ray source is configured to be movable close to and away from the center axis C along on the reference line L depending on the size of the tire, and for the Tire T2, the X-ray source is placed at the nearest position to the inner surface of the tread portion TR, where the predetermined elevation angle range β covers the angular range including both bead cores BC with the tread portion in between and it is at the nearest to the inner surface of the tread portion TR, as well.

At the same time, it is important to place the line-sensors 3, 4, 5 just adjacent to the outer surface of tire according to the size of the tire in order to obtain a image with high resolution, therefore, the line-sensors 3, 4, 5 positioned at positions 3m, 4m, 5m for photographing tire T1 are moved to the positions 3n, 4n, 5n for tire T2 as shown in FIG. 3.

For this purpose, for any tire size chosen from plural sizes of tire to be photographed, the line-sensors 3 and 4 are disposed within the said predetermined azimuth range α about the X-ray source which changes its position on the reference line L depending on the size of a tire, and at the same time, the line-sensors 3 and 4 are at the azimuth angular positions where they don't interfere with each other within the azimuth range α, therefore, they can get closer to the X-ray source 2 without interfering with each other, and this is the same for the relation between line-sensor 3 and 5.

Moreover, it is requisite that the line-sensors 3, 4, 5 are always kept so that the light receiving surface faces the X-ray source perpendicularly in the plane perpendicular to the longitudinal direction of each of the line-sensors 3, 4, 5 and including the X-ray source 2, in order to detect the transmission intensity distribution precisely, as already explained about the conventional technology.

Thus, X-ray photographing-tire apparatus 10 is configured to satisfy the condition that both of line-sensor 3 and line-sensor 4 (or line-sensor 5) are capable of getting very close to the outer surface of the tire of any size chosen from plural tire sizes without interfering with each other, and yet, the light receiving surface 3a, 4a, 5a are always kept to face the X-ray source perpendicularly wherever line-sensor 3 or line-sensor 4 is located. For this purpose, in the X-ray photographing-tire apparatus 10, the first line-sensor 3 is placed at the position deviated from the plane defined by both the reference line L and the center axis C, with such orientation that the light receiving surface 3a is tilted with the inclination of angle θ against the plane V which is defined as to be perpendicular to the reference line L, and is provided with two degrees of freedom of motion within the reference plane H, and the second and third line sensors 4, 5 are movable in the direction of the center axis C.

As to the two degrees of freedom of motion given to line-sensor 3 within the reference plane H, plural combinations of them are conceivable. In the embodiment exemplified in FIG. 3, with inclination angle θ of the light receiving surface to the plane V fixed as a predetermined value, two degrees of freedom within the reference plane H are to be a translational degree of freedom in the direction parallel with the reference line L and a translational degree of freedom in the direction close to and away from the X-ray source. That is, as shown in FIG. 3(b), the position 3m of line-sensor 3 is defined by the variable $x_{11}$ related to the translational degree of freedom in the direction parallel with the reference line L and the variable $a_1$ related to the translational degree of freedom in the direction close to and away from the X-ray source, in the same way, the position 3n of line-sensor 3 is defined by the variable $x_{12}$ related to the translational degree of freedom in the direction parallel with the reference line L and the variable $a_2$ related to the translational degree of freedom in the direction closer to and away from the X-ray source.

Figure 4:
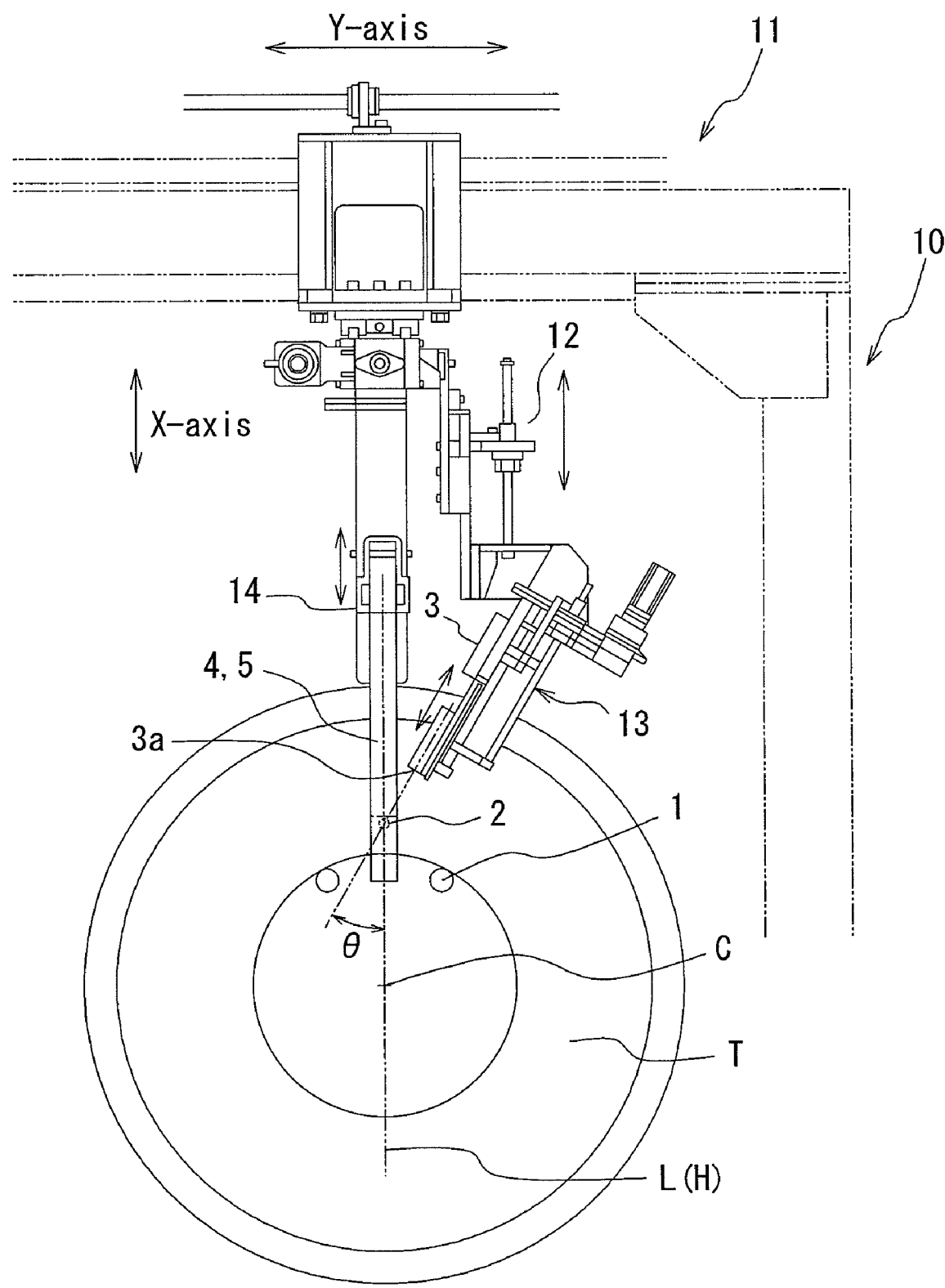
FIG. 4 is a front view showing a X-ray photographing-tire apparatus pertinent to present invention.

FIG. 4 is a front view of the apparatus showing a concrete example of the embodiment shown in FIG. 3. In the X-ray photographing-tire apparatus 10, the rotary device 1 to rotate a tire T about a horizontal center axis C, the X-ray source 2 located inside the tire T and emitting X-ray towards the inner surface of the tire T, the first line-sensor 3 detecting X-ray emitted towards the tread portion of the tire T, and the second and third line-sensor 4, 5 detecting X-ray emitted towards the sidewall portions are disposed as shown in FIG. 4. X-ray source 2 is movable on the reference line L vertically extended, by means of X-ray source transfer device (not shown).

Also, the line-sensors 3, 4, 5 are supported by a line sensor support-transfer device 11, the line sensor support-transfer device 11 comprises a first-sensor-X-axis-driving portion 12 for moving the line-sensor 3 along the reference line L in the direction of X-axis, a first-sensor-θ-axis-driving portion 13 for moving the line-sensor 3 mounted to the first-sensor-X-axis-driving portion 12 in the direction of θ-axis which is inclined to the reference line L by a predetermined angle θ, and a second-sensor-Z-axis-driving portion 14 for moving the line-sensors 4, 5 in the Z-axis parallel with the center axis C, and these driving portions 12, 13, 14 comprises such driving devices as electric motors, and linear guides to guide the motion of the line-sensors 3, 4, 5.

The line sensor support-transfer device 11 is configured to be movable in the direction of the Y-axis in order to avoid the interference with the tire T, and for the same purpose, the line-sensors 4, 5 are configured to be movable in the direction of X-axis.

In FIG. 4, the rotary device 1 is configured to support a tire with two rollers 1 and rotate the tire by rotating the rollers 1. The center line C of the tire mounted on the rotary device is specified as the line parallel with those rollers 1 within a plane of symmetry H, with reference to which two rollers are displaced symmetrically. With this configuration, the tire center line C moves up and down to the different position depending on the size of the tire within the plane H.

Figure 5:
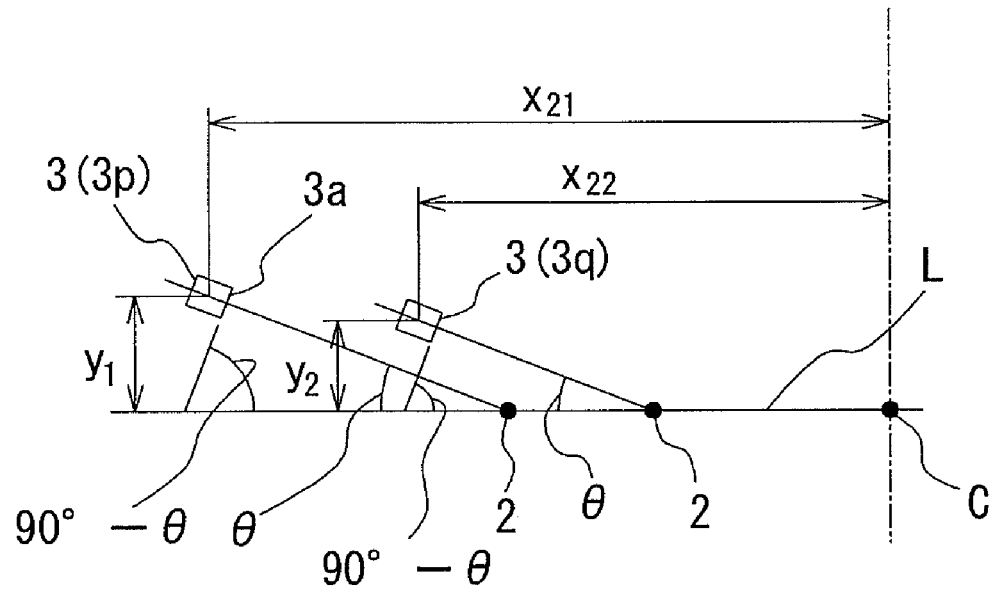
FIG. 5 is a layout of the line-sensors of another embodiment of a X-ray photographing-tire apparatus.
Figure 6:
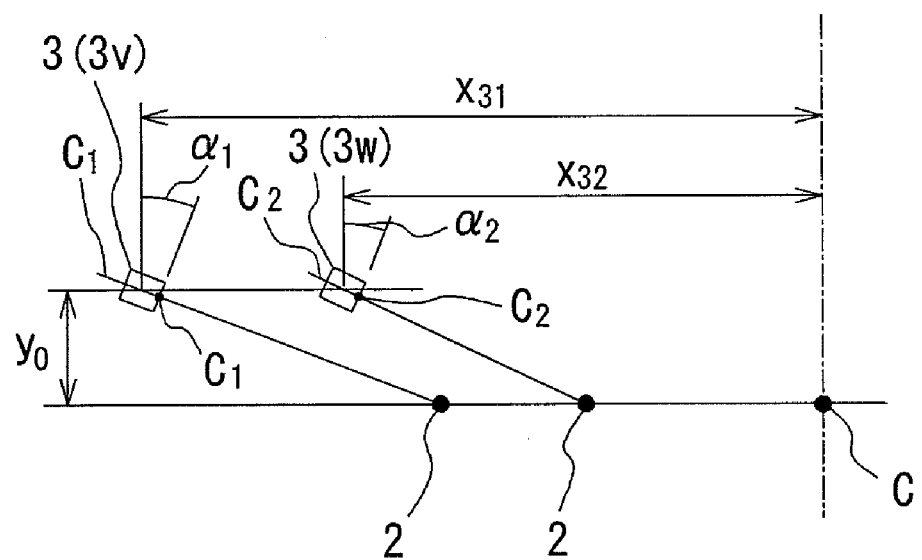
FIG. 6 is a layout of the line-sensors of another embodiment of a X-ray photographing-tire apparatus.

Other combinations with regard to the two degrees of freedom pertinent to line sensor 3 will be illustrated as follows. FIG. 5 and FIG. 6 are layouts showing the first line-sensor arrangement, regarding the paper plane as a plane perpendicular to the center axis C. In the embodiment shown in FIG. 5, with the inclination angle of the light receiving surface 3a of the line-sensor 3 to the reference line L being fixed to be as a predetermined value (90°−θ), two degrees of freedom pertinent to the line sensor 3 within the reference plane H comprises a translational degree of freedom in the direction parallel with the reference line L and a translational degree of freedom in the direction perpendicular to the reference line L. That is, the position 3p of the line sensor 3 is defined by a variable $x_{21}$ representing the position in the direction parallel with the reference line L and the variable $y_1$ representing the position in the direction perpendicular the reference line L, in the same way, the position 3q of the line sensor 3 is defined by a variable $x_{21}$ representing the position in the direction parallel with the reference line L and the variable $y_2$ representing the position in the direction perpendicular the reference line L.

In the embodiment shown in FIG. 6, those two degrees of freedom comprises a translational degree of freedom along on the line $L_d$ which is formed by moving the reference line L in parallel by predetermined amount and a rotational degree of freedom about the line parallel with the center axis C. That is, the line sensor 3 is movable keeping a distance $y_0$ from the reference line L constantly and the position 3v of the line-sensor 3 is represented by the variable $x_{31}$ representing the position in the direction parallel with the reference line L and the variable $α_1$, representing the orientation of the receiving surface 3a around the line $C_1$ which is parallel with the center axis C, in the same way, the position of 3w of the line-sensor 3 is represented by the variable $x_{21}$ representing the position in the direction parallel with the reference line L and the variable $α_2$ representing the orientation of the receiving surface 3a around the line $C_2$ which is parallel with the center axis C.

An apparatus for X-ray photographing a tire and method utilizing the apparatus, pertinent to the present invention can be applied to the various sizes of tire.

The invention claimed is:

1. An apparatus for X-ray photographing a tire, the apparatus comprising a rotary device for rotating a tire of any size chosen out of plural sizes with the center axis of the tire parallel with a given direction within a given plane, a point-like X-ray source emitting X-rays in an angular range specified by a predetermined azimuth range and a predetermined elevation angle range, and three linear line-sensors detecting a one dimensional X-ray intensity distribution by means of light receiving elements aligned in the longitudinal direction of each line-sensor, and producing a transmission X-ray image of the full circumference and full width of the tire, based on said one dimensional X-ray intensity distribution detected by said line-sensors for each angular position in tire rotation, characterized in that:

said X-ray source is oriented so that said predetermined azimuth range coincides with a predetermined angular range within a plane perpendicular to said given direction, said predetermined angular range including a reference line which is defined as the line perpendicular to said given direction and passing through the X-ray source, said X-ray source is movable along on said reference line according to the size of the tire mounted on the rotary device, so that said X-ray source can be placed at the nearest position to the inner surface of a tread portion of the tire as long as said predetermined elevation angle range covers the angular range including both bead cores with the tread portion in between, each of said three line-sensors is disposed so that at a plane perpendicular to a longitudinal direction of the respective line sensor and passing through the X-ray source, the light receiving surface of the corresponding light receiving elements is oriented perpendicular to a line headed to the X-ray source, a first line-sensor, being oriented parallel with said given direction, is placed within said predetermined azimuth range, in the radial outside of the tread portion of the tire mounted on the rotary device, second and third line-sensors, being disposed on the line formed by moving said reference line in parallel in said given direction, in the lateral outside of respective sidewall portions of the tire mounted on the rotary device, the first line-sensor is placed at the position deviated from the plane defined by both said reference line and said center axis, having two degrees of freedom of motion within a plane perpendicular to said given direction, so that the first line sensor can get as close as possible to the outer surface of the tread portion of the tire, according to the size of the tire mounted on the rotary device, keeping the orientation of said receiving surface of the first line-sensor perpendicular to the line headed to said X-ray source, and the second and third line-sensors are movable in the direction parallel with the center axis according to the size of the tire mounted on the rotary device, so that the second and third line-sensors can be as close as possible to respective sidewall portions of the tire.

2. An apparatus for X-ray photographing a tire according to claim 1, wherein said two degrees of freedom of motion pertinent to the first line-sensor comprises a translational degree of freedom along the line formed by moving said reference line in parallel, and a rotational degree of freedom around the line parallel with said given direction.

3. An apparatus for X-ray photographing a tire according to claim 1, wherein the inclination of the light receiving surface of the first line-sensor to said reference line is maintained constant and said two degrees of freedom of motion pertinent to the first line-sensor comprises a translational degree of freedom in the direction parallel with the reference line and a translational degree of freedom in the direction perpendicular to the reference line.

4. An apparatus for X-ray photographing a tire according to claim 1, wherein the inclination of the light receiving surface of the first line-sensor to said reference line is maintained constant and said two degrees of freedom of motion pertinent to the first line-sensor comprises a translational degree of freedom in the direction parallel with the reference line and a translational degree of freedom in the direction close to and away from the X-ray source.

5. A method for X-ray photographing a tire, the size of which is arbitrarily chosen from a predetermined group of sizes, utilizing the apparatus for X-ray photographing a tire according to claim 1, wherein said method comprises steps of: setting a tire onto the rotary device with the center axis oriented in said given direction, thereafter moving the X-ray source along on the reference line, so that X-ray source is placed at the nearest position to the inner surface of the tread portion of the tire as long as said predetermined elevation angle range covers the angular range including both bead cores with the tread portion in between, and moving the three line-sensors so that they get as close as possible to the outer surface of the tire, thereafter emitting X-ray from the X-ray source with tire rotating at a given rotational speed, and then finally acquiring transmission X-ray image of the tire.

\* \* \* \* \*